United States Patent
Williams et al.

[11] Patent Number: 6,113,638
[45] Date of Patent: Sep. 5, 2000

[54] METHOD AND APPARATUS FOR INTERVERTEBRAL IMPLANT ANCHORAGE

[76] Inventors: Lytton A. Williams, 72 Dapplegray La., Rolling Hills Estates, Calif. 90274; Robert G. Watkins, 410 Prospect Cir., South Pasadena, Calif. 91030

[21] Appl. No.: 09/259,503

[22] Filed: Feb. 26, 1999

[51] Int. Cl.[7] ............................... A61F 2/44; A61B 17/70
[52] U.S. Cl. .............................................. 623/17; 606/61
[58] Field of Search ........................... 623/17, 16; 606/61

[56] References Cited

U.S. PATENT DOCUMENTS

| | | | |
|---|---|---|---|
| 3,875,595 | 4/1975 | Froning | 3/1 |
| 4,309,777 | 1/1982 | Patil | 623/17 |
| 4,349,921 | 9/1982 | Kuntz | 3/1 |
| 4,401,112 | 8/1983 | Rezaian | 128/92 B |
| 4,501,269 | 2/1985 | Bagby | 128/92 G |
| 4,553,273 | 11/1985 | Wu | 623/18 |
| 4,554,914 | 11/1985 | Kapp et al. | 128/92 C |
| 4,627,853 | 12/1986 | Campbell et al. | 623/16 |
| 4,636,217 | 1/1987 | Ogilvie et al. | 623/17 |
| 4,678,470 | 7/1987 | Nashef et al. | 623/16 |
| 4,714,469 | 12/1987 | Kenna | 623/17 |
| 4,743,256 | 5/1988 | Brantigan | 623/17 |
| 4,743,259 | 5/1988 | Bolander et al. | 623/16 |
| 4,759,769 | 7/1988 | Hedman et al. | 623/17 |
| 4,834,757 | 5/1989 | Brantigan | 623/17 |
| 4,863,476 | 9/1989 | Shepperd | 623/17 |
| 4,878,915 | 11/1989 | Brantigan | 623/17 |
| 4,932,975 | 6/1990 | Main et al. | 623/17 |
| 4,961,740 | 10/1990 | Ray et al. | 606/61 |
| 4,997,432 | 3/1991 | Keller | 606/61 |
| 5,015,247 | 5/1991 | Michelson | 606/61 |
| 5,026,373 | 6/1991 | Ray et al. | 606/61 |
| 5,055,104 | 10/1991 | Ray | 606/61 |
| 5,059,193 | 10/1991 | Kuslich | 606/61 |
| 5,062,850 | 11/1991 | MacMillan et al. | 623/17 |
| 5,071,437 | 12/1991 | Steffe | 623/17 |
| 5,123,926 | 6/1992 | Pisharodi | 623/17 |
| 5,147,402 | 9/1992 | Bohler et al. | 623/16 |
| 5,192,327 | 3/1993 | Brantigan | 623/17 |
| 5,236,460 | 8/1993 | Barber | 623/17 |
| 5,258,031 | 11/1993 | Salib et al. | 623/17 |
| 5,263,953 | 11/1993 | Bagby | 606/61 |
| 5,290,312 | 3/1994 | Kojimoto et al. | 623/17 |
| 5,306,310 | 4/1994 | Siebels | 623/17 |
| 5,314,477 | 5/1994 | Marnay | 623/17 |
| 5,336,223 | 8/1994 | Rogers | 606/61 |
| 5,397,364 | 3/1995 | Kozak et al. | 623/17 |
| 5,401,269 | 3/1995 | Buttner-Janz et al. | 623/17 |
| 5,417,975 | 5/1995 | Lussi et al. | 424/423 |
| 5,425,769 | 6/1995 | Snyders, Jr. | 623/16 |
| 5,439,684 | 8/1995 | Prewett et al. | 424/422 |
| 5,455,231 | 10/1995 | Constantz et al. | 514/21 |

(List continued on next page.)

FOREIGN PATENT DOCUMENTS

| | | | |
|---|---|---|---|
| 0 188 954 A1 | 7/1986 | European Pat. Off. | A61F 5/02 |
| 0 425 542 B1 | 5/1991 | European Pat. Off. | A61F 2/44 |
| 000538183 | 4/1993 | European Pat. Off. | 623/17 |
| 0610837 | 8/1994 | European Pat. Off. | 623/17 |
| 44 16 605 C1 | 6/1995 | Germany | A61F 2/44 |
| 091013598 | 9/1991 | WIPO | 623/17 |
| WO 92/14423 | 9/1992 | WIPO | A61F 2/44 |
| 094004100 | 3/1994 | WIPO | 623/17 |
| WO 97/00054 | 3/1997 | WIPO | A61F 2/44 |

*Primary Examiner*—Paul J. Hirsch
*Assistant Examiner*—Michael B. Priddy
*Attorney, Agent, or Firm*—David J. Weitz; Wilson Sonsini Goodrich & Rosati

[57] ABSTRACT

Methods and devices are provided for intervertebral implant anchorage. An implantable device for insertion into an intradiscal section between adjacent vertebrae is provided. The implantable device includes at least one anchor plate which comprises a plate member sized to be positioned within an intradiscal section between adjacent vertebrae and a plurality of anchoring elements extending from a surface of the plate member, each anchoring element including a distal portion capable of being introduced into the vertebra through the vertebral end plate; and an intradiscal component coupled to the anchor plate.

32 Claims, 20 Drawing Sheets

U.S. PATENT DOCUMENTS

| | | | |
|---|---|---|---|
| 5,464,439 | 11/1995 | Gendler | 623/16 |
| 5,507,813 | 4/1996 | Dowd et al. | 623/16 |
| 5,507,816 | 4/1996 | Bullivant | 623/17 |
| 5,510,396 | 4/1996 | Prewett et al. | 523/113 |
| 5,522,899 | 6/1996 | Michelson | 623/17 |
| 5,534,030 | 7/1996 | Navarro et al. | 623/17 |
| 5,549,679 | 8/1996 | Kuslich | 623/17 |
| 5,554,191 | 9/1996 | Lahille et al. | 623/17 |
| 5,585,116 | 12/1996 | Boniface et al. | 424/549 |
| 5,609,635 | 3/1997 | Michelson | 623/17 |
| 5,645,591 | 7/1997 | Kuberasampath et al. | 623/16 |
| 5,653,763 | 8/1997 | Errico et al. | 623/17 |
| 5,658,335 | 8/1997 | Allen | 623/17 |
| 5,665,122 | 9/1997 | Kambin | 623/17 |
| 5,676,701 | 10/1997 | Yuan et al. | 623/17 |
| 5,683,465 | 11/1997 | Shinn et al. | 623/17 |
| 5,693,100 | 12/1997 | Pisharodi | 623/17 |
| 5,702,391 | 12/1997 | Lin | 606/61 |
| 5,702,450 | 12/1997 | Bisserie | 623/17 |
| 5,702,455 | 12/1997 | Saggar | 623/17 |
| 5,713,904 | 2/1998 | Errico et al. | 606/73 |
| 5,749,916 | 5/1998 | Richelsoph | 623/17 |
| 5,776,199 | 7/1998 | Michelson | 623/17 |
| 5,782,832 | 7/1998 | Larsen et al. | 606/61 |
| 5,800,550 | 9/1998 | Sertich | 623/17 |
| 5,888,227 | 3/1999 | Cottle | 623/17 |
| 5,899,941 | 5/1999 | Nishijima et al. | 623/17 |
| B1 4,961,740 | 1/1997 | Ray et al. | 606/61 |

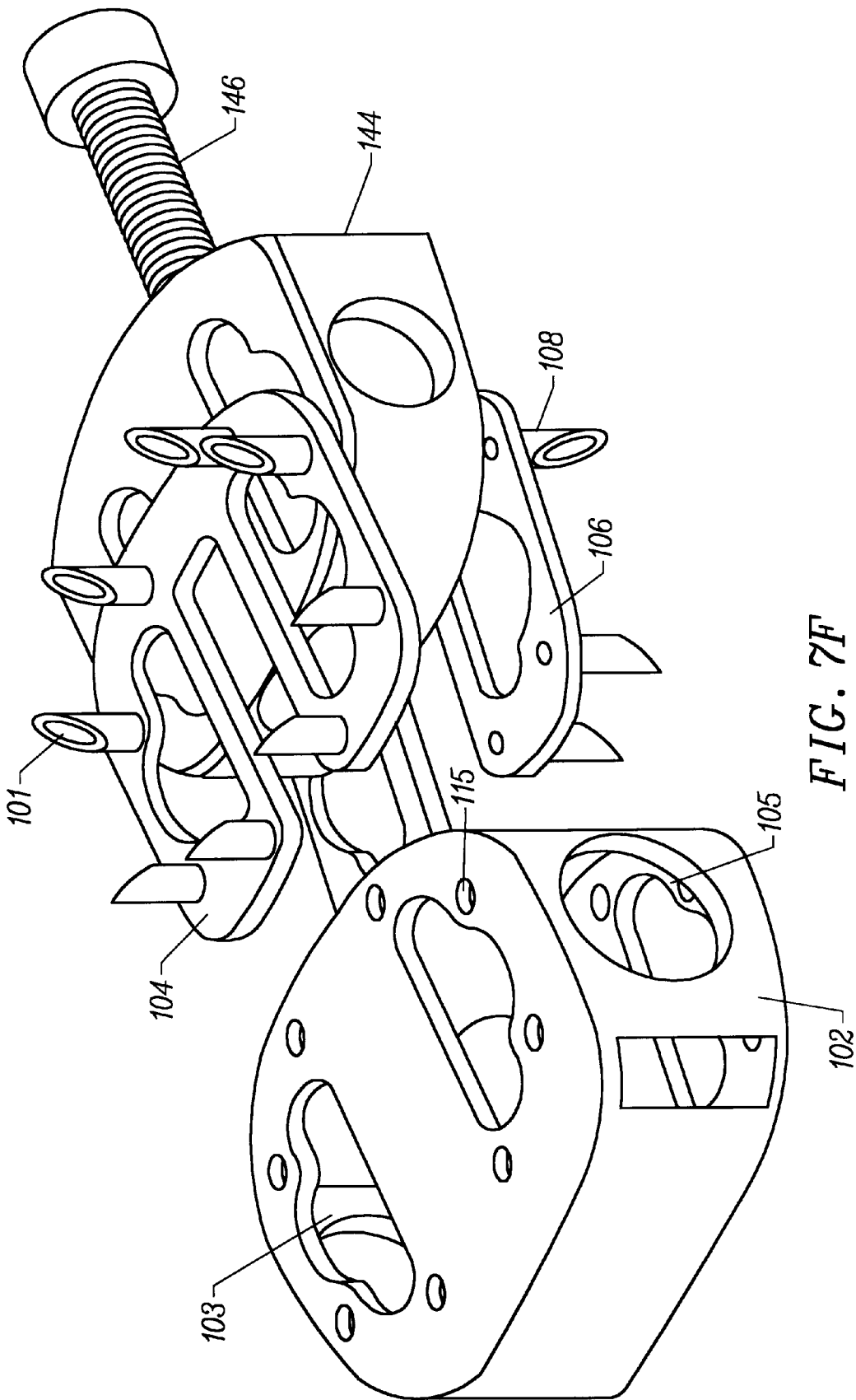

FIG. 9A  FIG. 9A1

METHOD AND APPARATUS FOR INTERVERTEBRAL IMPLANT ANCHORAGE

FIELD OF THE INVENTION

The present invention relates to methods and devices for treating intervertebral disc diseases and more particularly to intervertebral prostheses for positioning in an intervertebral space to treat intervertebral disorders.

BACKGROUND OF THE INVENTION

Back pain remains a major public health problem, especially among aged people. Persistent and severe back pain often causes debility and disability, and such a pain is closely associated with intervertebral disc abnormalities of the spine.

The human spine is a flexible structure comprised of thirty-three vertebrae. Intervertebral discs separate and cushion adjacent vertebrae, and act as shock absorbers and allow bending between the vertebrae. An intervertebral disc comprises two major components: the nucleus pulposus and the annulus fibrosis. The nucleus pulposus is centrally located in the disc and occupies 25–40% of the disc's total cross-sectional area. The annulus fibrosis surrounds the nucleus pulposus and resist torsional and bending force applied to the disc. Vertebral end-plates separate the disc from the vertebrae on either side of the disc.

Because of exertion, injury, illness, accident or abuse, one or more of the vertebrae and/or one or more discs may become damaged and malfunctioning. Specifically, disorders of the vertebrae and discs include but are not limited to 1) disruption of the disc annulus such as annular fissures; 2) chronic inflammation of the disc; 3) localized disc herniations with contained or escaped extrusions; and 4) relative instability of the vertebrae surrounding the disc.

Various approaches have been developed to treat back pain. Minor back pain can be treated with medication and other non-invasive therapy. However, it is often necessary to remove at least a portion of the damaged and/or malfunctioning back component. For example, when a disc becomes ruptured, the ruptured disc may be surgically removed and the two vertebrae between the removed disc fuse together. In one approach, the end plates of two adjacent vertebra are fused posterior-laterally by screws. However, such posterior fusion with rigid end-plate fusion can be associated with pseudoarthrosis.

To promote fusion or arthrodesis across the intradiscal space, intervertebral implants are used to support and fuse together adjacent vertebrae by posterior-fusion or anterior grafting. For example, surgical prosthetic implants for vertebrae described in U.S. Pat. No. 5,827,328 include rigid annular plugs that have ridged faces to engage adjacent vertebrae to resist displacement and allow ingrowth of blood capillaries and packing of bone graft. These annular implants are usually made of biocompatible carbon fiber reinforced polymers, or traditional orthopaedic implant materials such as nickel, chromium, cobalt, stainless steel or titanium. The individual implants are internally grooved and are stacked against each other to form a unit between the two adjacent vertebrae. One of the disadvantages of these interlocked implants is that, the implants may not be stable enough to withstand rotation and may lead to implant loosening and failure of the prosthesis.

Another intervertebral fusion device described by Kozak, et al. (U.S. Pat. No. 5,397,364) includes an assembly of two lateral spacers and two central spacers, which defines a channel in the center of the fusion device for insertion of the bone graft material. The spacers are maintained in their configuration within the intradiscal space by screws threaded into a vertebra from the outside of the disc. A disadvantage of this device is a tendency for the anchoring screws to become dislodged.

SUMMARY OF THE INVENTION

An anchoring plate is provided for anchoring an intradiscal device to an end plate of a vertebra. The anchoring plate includes a plate member sized to be positioned within an intradiscal section between adjacent vertebrae and a plurality of anchoring elements extending from a surface of the plate member, each anchoring element including a distal portion capable of being introduced into the vertebra through the vertebral end plate. In one embodiment, at least one of the anchoring elements includes a lumen. The lumen allows ingrowth of the bone graft material through the lumen to the end-plate of the vertebra. The lumen preferably has a diameter between about 0.5 mm–9 mm.

An implantable device for insertion into an intradiscal section between adjacent vertebrae is also provided which includes an anchor plate comprising of a plate member sized to be positioned within an intradiscal section between adjacent vertebrae and a plurality of anchoring elements extending from a surface of the plate member, each anchoring element including a distal portion capable of being introduced into an end plate of one of the adjacent vertebrae; and an intradiscal component coupled to the anchor plate. In one embodiment, the intradiscal component includes a spacer separating the anchor plate from the end plate of the other adjacent vertebra. In another embodiment, the intradiscal component includes a cage having a first side for positioning adjacent a first vertebra and a second side for positioning adjacent a second vertebra, the first side including a plurality of holes through which the anchoring elements on the anchor plate can be positioned, and the second side including at least one hollow bore for ingrowth of bone material. In yet another embodiment, the intradiscal component includes an artificial disc.

Another implantable device for insertion into an intradiscal section between adjacent vertebrae is provided which includes a first anchor plate comprising a plate member sized to be positioned within an intradiscal section adjacent a first vertebrae and a plurality of anchoring elements extending from a surface of the plate member, each anchoring element including a distal portion capable of being introduced into an end plate of the first vertebra; a second anchor plate comprising a plate member sized to be positioned within an intradiscal section adjacent a second vertebrae and a plurality of anchoring elements extending from a surface of the plate member, each anchoring element including a distal portion capable of being introduced into an end plate of the second vertebra; and an intradiscal component coupled to the first and second anchor plates. In one embodiment, the intradiscal component includes a spacer separating the first anchor plate from the second anchor plate. In another embodiment, the intradiscal component includes a cage having a first side for positioning adjacent the first vertebra and a second side for positioning adjacent the second vertebra, the first and second sides each including a plurality of holes through which the anchoring elements on the first and second anchor plates can be positioned. In yet another embodiment, the intradiscal component includes an artificial disc.

A method is also provided for anchoring an implantable device within an intradiscal section between adjacent vertebrae which includes:

creating a space between adjacent vertebrae;

inserting into the space created an intradiscal device comprising an anchor plate comprising a plate member sized to be positioned within the space and a plurality of anchoring elements extending from a surface of the plate member, each anchoring element including a distal portion capable of being introduced into an end plate of one of the adjacent vertebrae; and causing the anchoring elements on the anchor plate to be introduced into the vertebrae through the vertebral end plate.

In one embodiment according to the method, the anchoring elements are introduced into the vertebrae by applying a force to the anchor plate, anchor plate having a vector positioned entirely within the intradiscal space. In one variation, the force is applied to the anchor plate approximately perpendicular to a plane of the end plate, In another embodiment, the anchoring elements are introduced into the vertebrae without rotating the anchor elements.

In yet another embodiment, the anchoring elements are introduced into the vertebrae without first creating one or more holes in the vertebrae for the anchoring elements.

In yet another embodiment, the implantable device includes an intradiscal component. Examples of intradiscal components include an intradiscal spacer, a cage, and an artificial disc.

In yet another embodiment, the implantable device includes first and second anchor plates. Inserting the intradiscal device includes positioning the first anchor plate adjacent a first of the adjacent vertebra and positioning the second anchor plate adjacent a second of the adjacent vertebra. Causing the anchoring elements to be introduced into vertebrae includes causing anchoring elements on the first anchor plate to be introduced into the first vertebra and causing anchoring elements on the second anchor plate to be introduced into the second vertebra.

In the apparatuses and methods of the present invention, the plate member preferably has a non-smooth surface so as to promote ingrowth of bone material on the surface. The plate member also preferably has at least one hollow bore through the plate to allow ingrowth of bone material through the plate to the end plate of the vertebra.

The anchoring elements can have a plurality of shapes including cone, cylinder, triangle, square, rectangle and other irregular shapes so long as the anchoring elements are capable of being introduced into an end plate of a vertebra. The anchoring elements can extend from the plate member substantially vertically, angularly or curved. The anchoring elements are preferably shaped so as to minimize the risk of splintering the vertebra by introducing the anchoring elements into the vertebra.

The apparatuses and methods of the present invention may be used for a variety of medical procedures in spine surgery. For example, the anchor plate may be used to secure an implant inserted between adjacent vertebrae, the implant including bone grafts, artificial annular plugs, compressible fusion material, artificial intravertebral disc or other prosthetic devices. The implantable device may be used to replace the damaged and/or malfunctioning intravertebral disc with an artificial disc attached to the anchor plate on the device, or to replace the whole vertebral body with an artificial vertebra which is biomechanically compatible to the spine. The implantable device can be customized to the individuals being treated. In one embodiment, the anchor plate has substantially the shape of a naturally-occurring intervertebral disc and the size of the patient's disc.

Additional advantages of the present invention are set forth in the description which follows.

BRIEF DESCRIPTION OF THE DRAWINGS

FIG. 5A is a side view of the implantable device.

FIG. 5B is a sagittal view the implantable device.

FIG. 5C is a sagittal view of an anchor plate of the implantable device.

FIG. 5D is a sagittal view of a spacer inside of the implantable device.

FIGS. 7 A–E illustrate assembly of an implantable device.

FIG. 7F illustrates assembly of the implantable device illustrated in FIGS. 5A–D.

FIGS. 9A–D illustrate a method for implanting an implantable device according to the present invention.

FIG. 9A illustrates inserting a spacer between two adjacent vertebrae.

FIG. 9B illustrates putting a guide over the spacer.

FIG. 9C illustrates inserting an implantable device into the guide.

FIG. 9D illustrates using a wedge spreader to introduce anchoring elements into the end plate of the vertebra.

DETAILED DESCRIPTION OF THE PREFERRED EMBODIMENT

The present invention relates to devices which may be anchored to vertebrae of the spine by introducing anchoring elements through an end plate of the vertebrae. In particular, an anchoring plate, which comprises a plurality of anchoring elements such as spikes or prongs extending from the plate, is provided for anchoring an intradiscal device to an end plate of a vertebra. By securing the anchor plate to an end plate of the vertebra, a surgeon operating on a patient's spine can attach a variety of intradiscal components to the anchor plates. The secured anchorage and support provided by the apparatus of the present invention prevents loosening of the apparatus and enhances the fusion of the adjacent vertebrae.

A variety of intradiscal components can be incorporated into the apparatus of the present invention. In one embodiment, the intradiscal component includes a cage within which the anchor plate is contained. Bone graft material can be filled into the cage which is attached to and stabilized by the anchor plate on an end plate of a vertebra, thereby promoting bone ingrowth through the holes on the cage. Alternatively, an artificial intravertebral disc can be included in the apparatus.

It should be noted that other intervertebral fusion devices may also be attached to the anchor plate for restoring or maintaining the normal geometry of the intradiscal space, such as disc height and sagittal angle. Moreover, an artificial vertebral body which is biomechanically compatible with the spine may be attached to the anchor plate to replace a damaged vertebra and restore normal functions to the spine.

Figure 1:
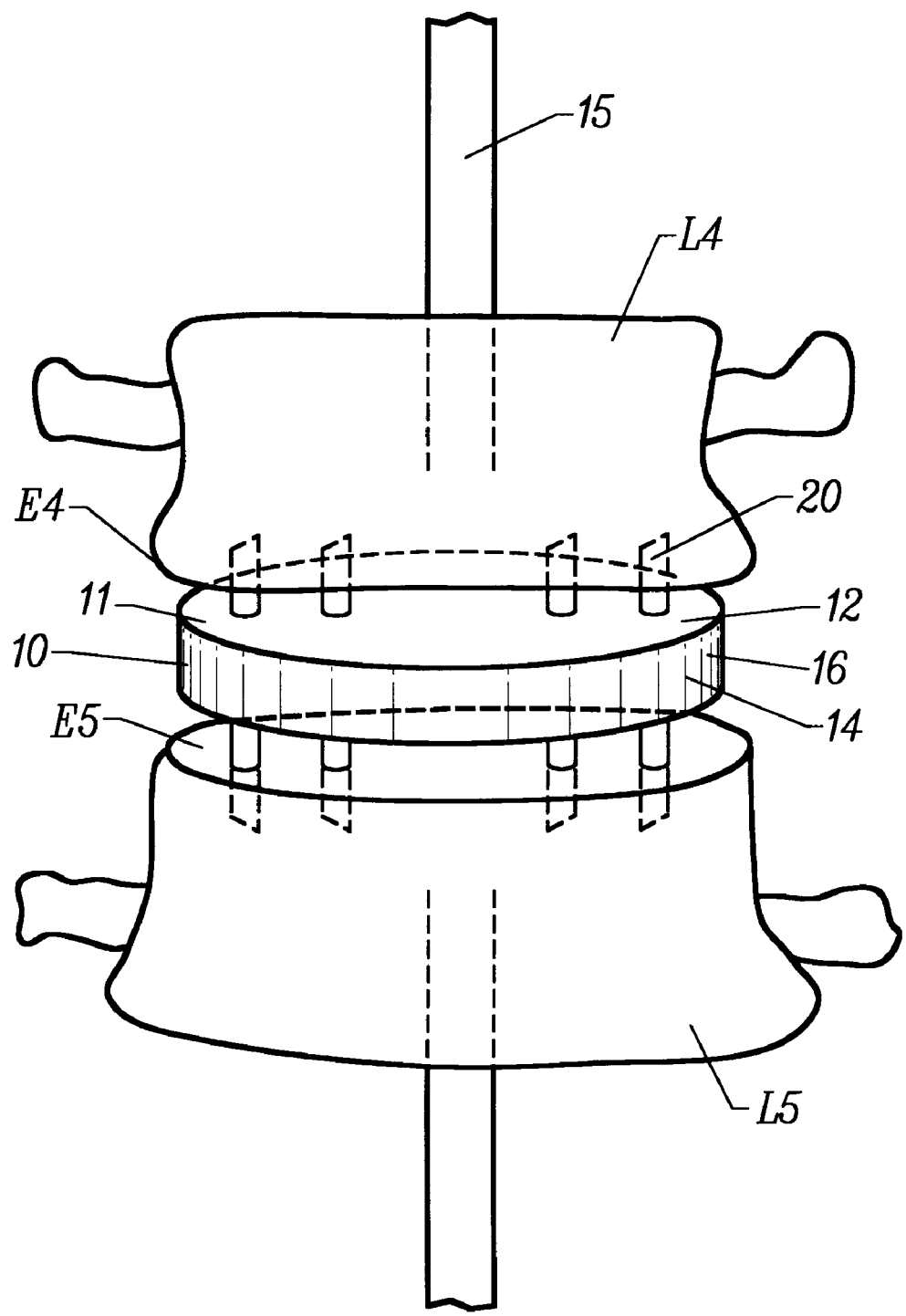
FIG. 1 illustrates an implantable device according to the present invention.

One embodiment of the invention is illustrated in FIG. 1, showing a frontal view of an implantable device 10 inserted between two adjacent vertebrae L4 and L5. In this embodiment, the implantable device 10 includes a first anchor plate 12, a second anchor plate 14 and an intradiscal component 16. Each of the first and second anchor plates includes an anchor plate and a plurality of anchoring elements 20 extending from a surface 11 of the plate member 18. The anchoring elements 20 on each of the anchor plates 12 and 14 are introduced into vertebrae L4 and L5 through end plates E4 and E5 of vertebrae L4 and L5, respectively. This embodiment of the implantable device has a size approximating the intradiscal space between adjacent vertebrae. This device is particularly suitable for positioning via an anterior approach. Because intervertebral discs are located in front of the spine and anterior to the spinal cord 15, prosthetic operations such as disc replacement through an anterior approach eliminates the need to remove or retract nerve, thus reducing the risk of nerve injury.

Figure 2:
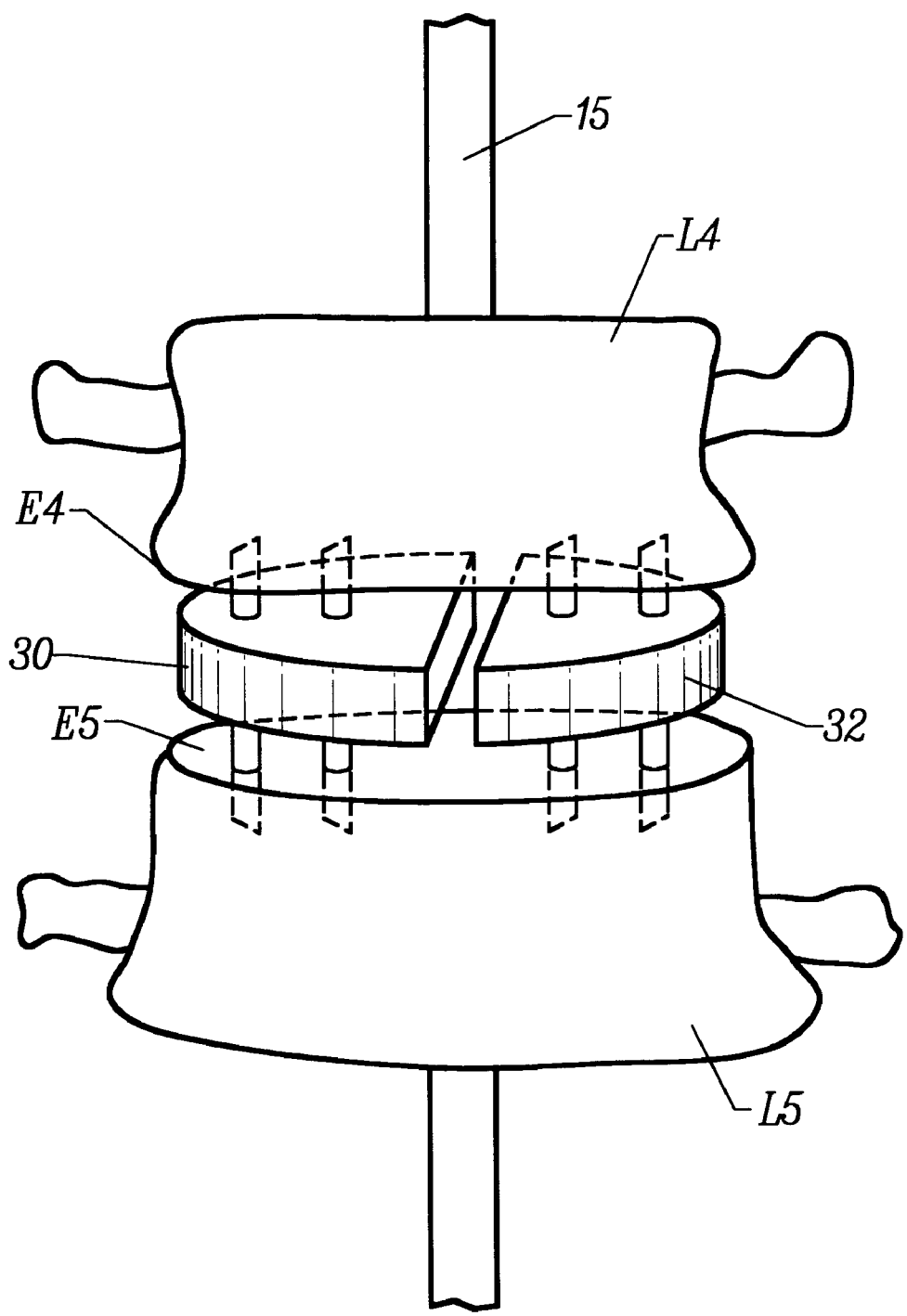
FIG. 2 illustrates two hemi-implantable devices.

Alternatively, the implantable device according to the present invention may also be sized to a hemicircle or hemioval. As illustrated in FIG. 2, two hemioval implantable devices 30 and 32 can be used to approximate the intradiscal space and conform with the general outline perimeter of the vertebrae. Such an implantable device with a hemioval size allows better access to the posterior portion of the spine when the devices are implanted through a posterior approach. For example, the first hemi-device 30 can be inserted into and fill in half of the intradiscal space without colliding with the spinal cord 15, then followed by placing the second hemi-implantable device 32 to fill in the other half of the intradiscal space. Similar to the implantable device 10 illustrated in FIG. 1, the anchoring elements on the hemi-implantable device are introduced into the end plate E4 and E5 of the vertebrae L4 and L5, respectively. Bone graft material or artificial disc can be put into the device for posterior-lateral fusion or rigid posterior instrumentation. Positioning the bone graft material between first and second anchor plates 12, 14 to attain fusion and prevent the anchor plates from being dislodged from the vertebrae.

Figure 3A:
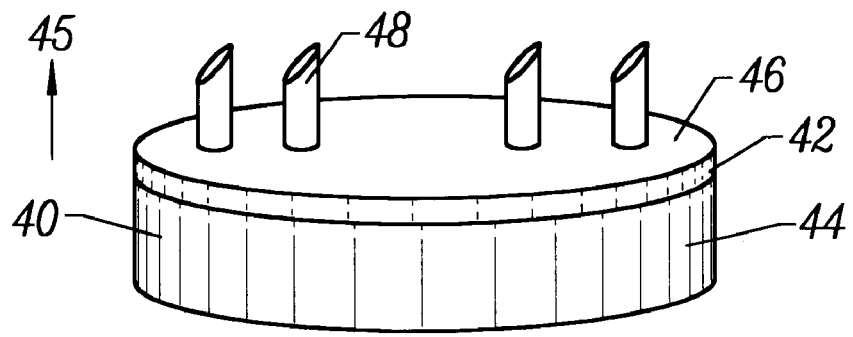
FIG. 3A illustrates an implantable device having anchoring elements extending from one side of the device.

In another embodiment, as illustrated in FIG. 3A, the implantable device 40 includes an anchor plate 42 and an intradiscal component 44. The anchor plate 42 includes a plate member 46 and a plurality of anchoring elements 48 extending from the plate member 46. The anchoring elements 48 can be introduced into an end plate of a vertebra by applying a force in a direction 45 approximately perpendicular to the end plate, thereby securing the device 40 within an intradiscal space. In this regard, the force applied to the anchoring elements may have a vector positioned entirely within the intradiscal space.

Figure 3B:
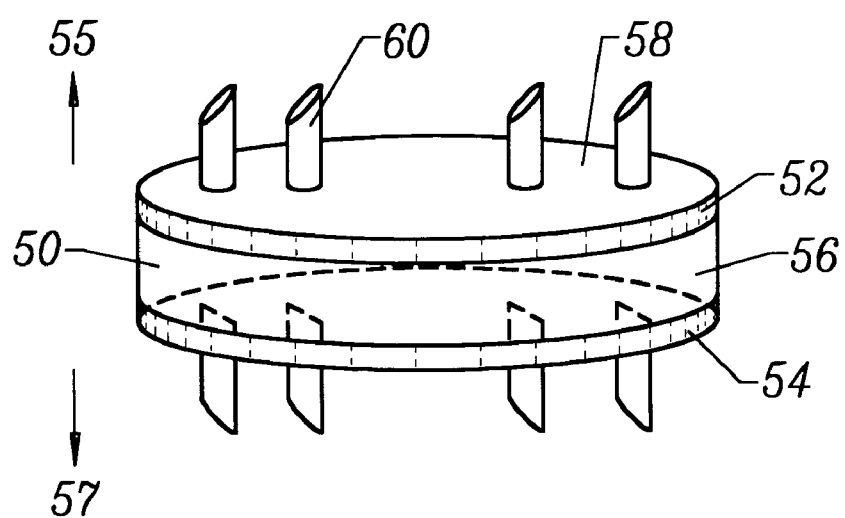
FIG. 3B illustrates an implantable device having anchoring elements extending from opposing sides of the device.

In yet another embodiment, as illustrated in FIG. 3B, an implantable device 50 includes a first anchor plate 52, a second anchor plate 54 and an intradiscal component 56. Each of the first and second anchor plates 52 and 54 includes a plate member 58 and a plurality of anchoring elements 60 extending from the plate member 58. The anchoring elements 60 on anchor plate 52 can be introduced into an end plate of a vertebra in directions 55, 57 approximately perpendicular to the end plates, thereby securing the device 50 within an intradiscal space between the two adjacent vertebrae.

Figure 4:
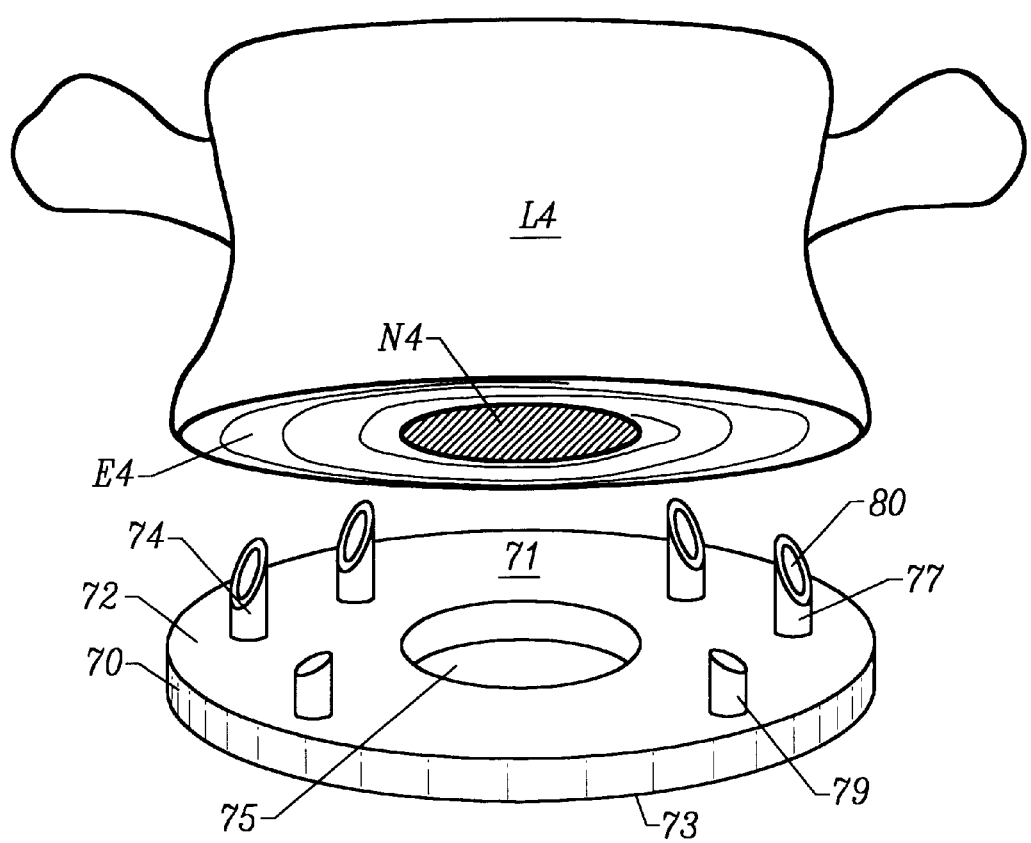
FIG. 4 illustrates an embodiment of an anchor plate

An illustration of an embodiment of an anchor plate is illustrated in FIG. 4. In this embodiment, the anchor plate 70 includes a plate member 72 and a plurality of anchoring elements 74 extending from a surface 71 of the plate member 72. It is preferred that a plate member 72 has at least one hollow bore or hole 75 through surface 71 and 73 of the plate member 72 to allow bone ingrowth through the hole 75 to the end plate E4 of vertebra L4, thereby enhancing fusion of adjacent vertebrae. The hole 75 may be positioned such that the hole is adjacent nucleus pulposus N4 of the operative intravertebral disc when the device is positioned intervertebrally. The hole is preferably smaller than and optionally as large as the nucleus pulposus N4. This positioning and sizing of the hole 75 allows fusion of bone graft material with a weaker portion of the vertebra known to be highly vascular and biological active.

The anchor plate 70 includes at least two anchoring elements 74 distributed on the surface 71 of the plate member 72. The anchor plate may have any regular shape: round, square, rectangle, elliptical, or an irregular shape. The anchor plate is preferred to have a surface area between about 5 mm$^2$–40 mm$^2$; and a thickness preferably between about 1 mm–10 mm, more preferably about 5 mm.

The anchoring elements 74 are preferred to be sharp spikes having a cone, cylinder, square or rectangle shape. The height and width of the anchoring elements are preferably between about 0.5 mm–15 mm, 0.3 mm–15 mm, respectively.

In a preferred embodiment, the anchoring element 74 includes a lumen 80. The lumen preferably has a diameter between about 0.5 mm–9 mm. The lumen allows ingrowth of the bone graft material through the lumen to the end-plate of the vertebra. The lumen also facilitates entry of the anchoring element into the end plate without splintering the vertebra. The surface of the lumen is preferably rough.

The distal portion 77 of the anchoring element 74 may be straight or curved. The surface 79 of the anchoring element 12 is preferred to have a smooth outer surface to facilitate penetration of the element 74 into the end plate E4. In particular, the surface 79 of the anchoring element 74 is preferred not to have a thread for screwing the element 74 into the end plate E4.

The anchoring elements 74 may extend from the plate member 11 substantially vertically, angularly or curved. The direction of the force used to cause the anchoring elements to enter the vertebra will depend on the shape and angular positioning of the anchoring elements.

The materials used to construct the anchor plate and the implantable device are preferred to be able to endure the stresses and environment to which a vertebra implant is subjected. In addition, such materials should be biocompatible, and substantially chemically inert so as not to cause any detrimental effect to the patient in whom the device is implanted. The anchor plate and implantable device may be made of radiolucent material such as carbon fiber reinforced polymers known commercially as "Peek" (polyetherether ketone) or "Ultrapek" (polyether ketone, ether ketone, ketone), polycarbonate, polypropylene, polyethylene and polysulfone plastics material filled with glass or carbon fibers, or traditional orthopaedic implant material such as nickel stainless steel, titanium alloy, heavy plastic polymer, ceramic, etc. One of ordinary skill in the art will recognize other suitable materials, for example, a cobalt-chromium alloy or a titanium alloy having 4% vanadium and % aluminum, ceramic material such as aluminium oxide and zirconium oxide. The surface 71 of the anchor plate 70 is preferred to be rough to potentiate bone ingrowth on the side of the plate contacting the end plate E4 of the vertebra L4, thereby strengthening the anchorage to the end plate. The surface 73 of the anchor plate 70 may be porous coated or coated with hydroxyapatite or bioactive proteins (e.g. bone morphogenic protein) to promote bone ingrowth.

Figure 5A:
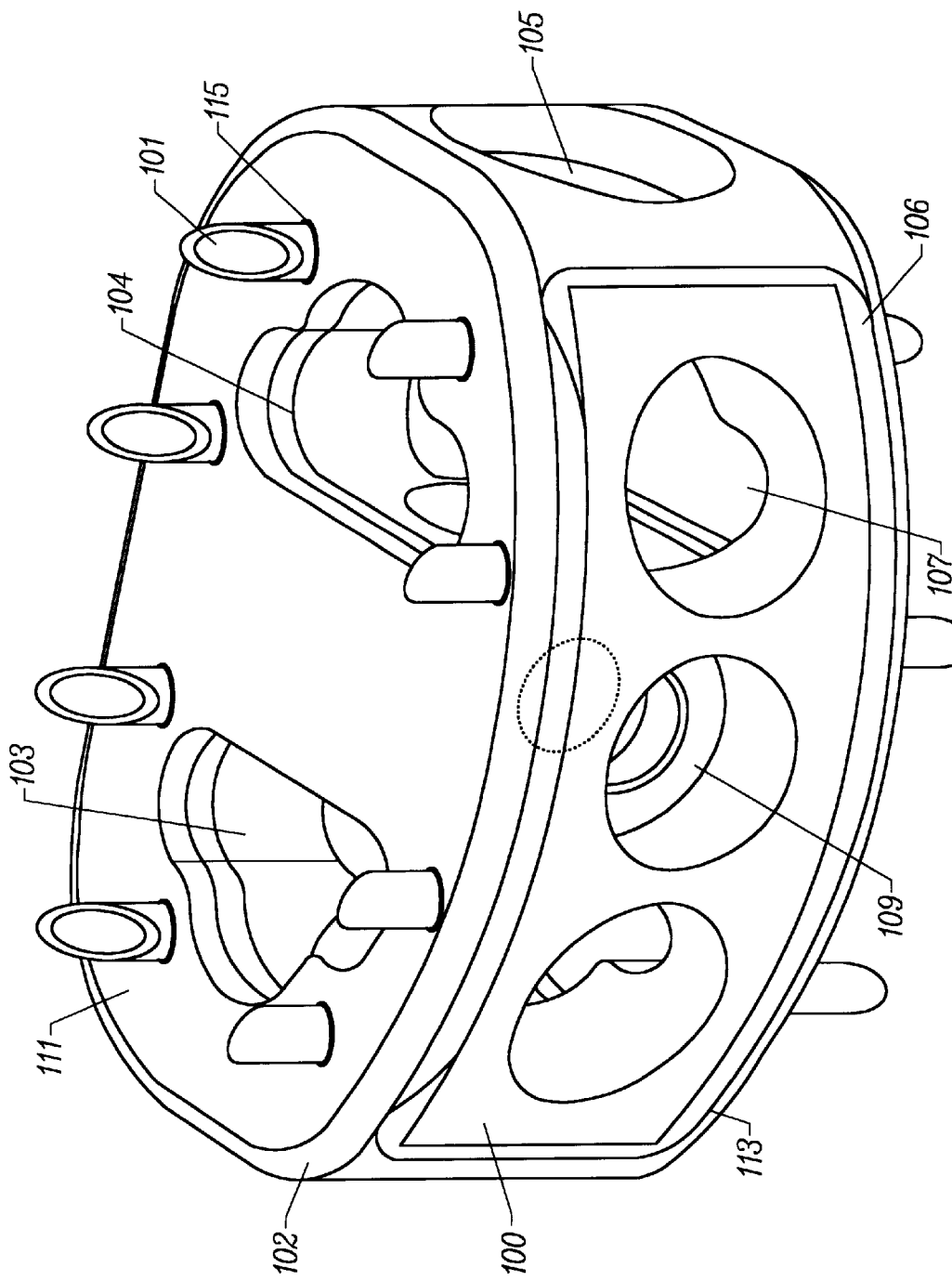
FIGS. 5A–D illustrate an implantable device having a cage.

FIGS. 5A–D illustrate a preferred embodiment of an implantable device. As illustrated in FIG. 5A, the implantable device 100 includes an intradiscal component—a cage 102, a first anchor plate 104 and a second anchor plate 106 contained within the cage 102. A plurality of anchoring elements 108 on each of the anchor plates 104 and 106 extend from the anchor plates and through holes 115 on the surfaces 111 and 113, respectively of the cage 102. The cage 102 includes intervertebral lateral channels 105 and frontal channels 107 which are adapted to receive bone graft material therein. In addition, channel 109 is configured to receive a screw therethrough for causing the anchoring elements 108 to be pushed into the end plates of adjacent vertebrae.

Figure 5B:
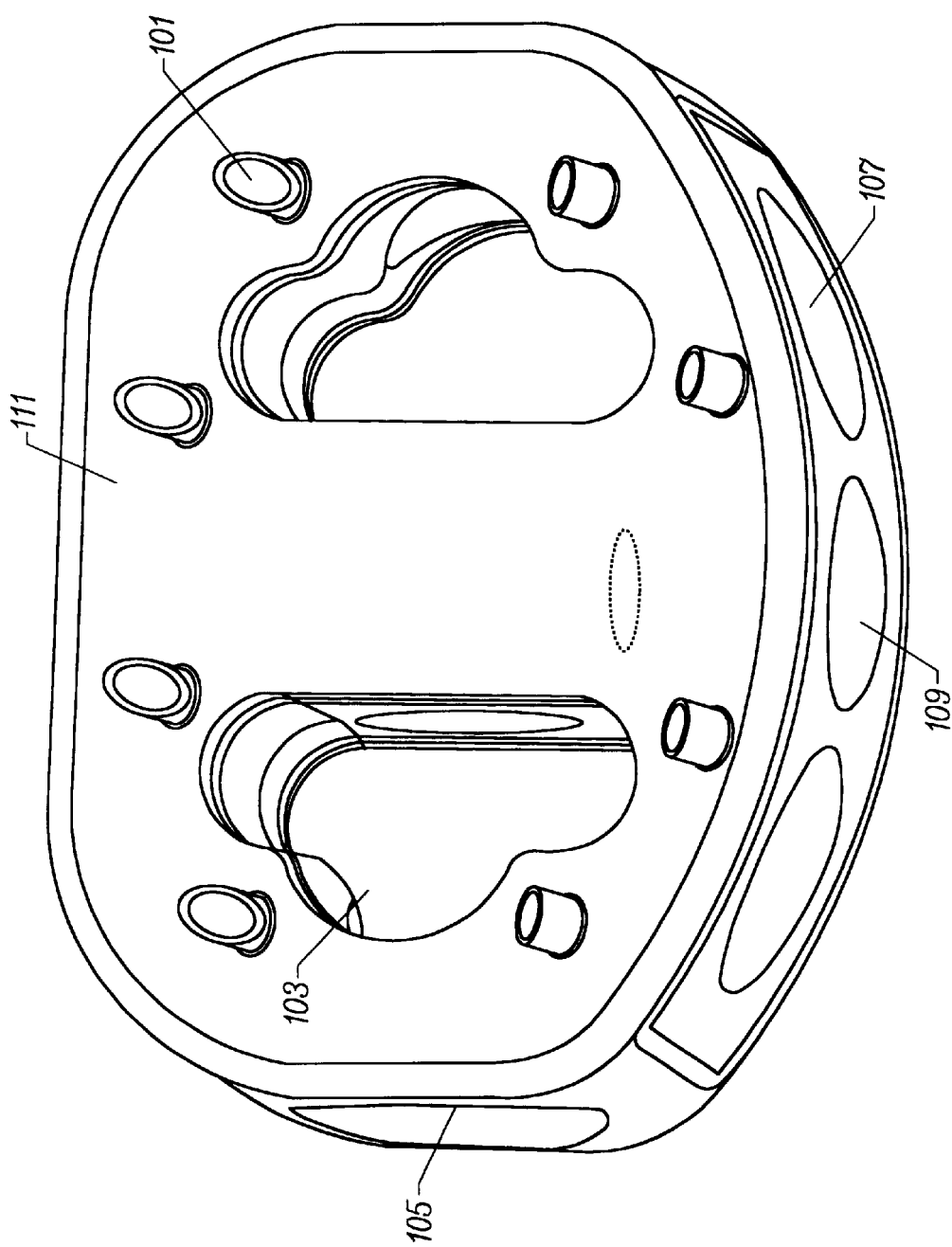

FIG. 5B is a sagittal view of the implantable device 100. The surface 111 of cage 102 contacts an end plate of a vertebra and is preferred to be porous and coated with hydroxyapatite or bone morphogenic protein to promote bone ingrowth. As illustrated, anchoring elements 108 with lumen 101 extend through holes 115 in the cage 102.

Figure 5C:
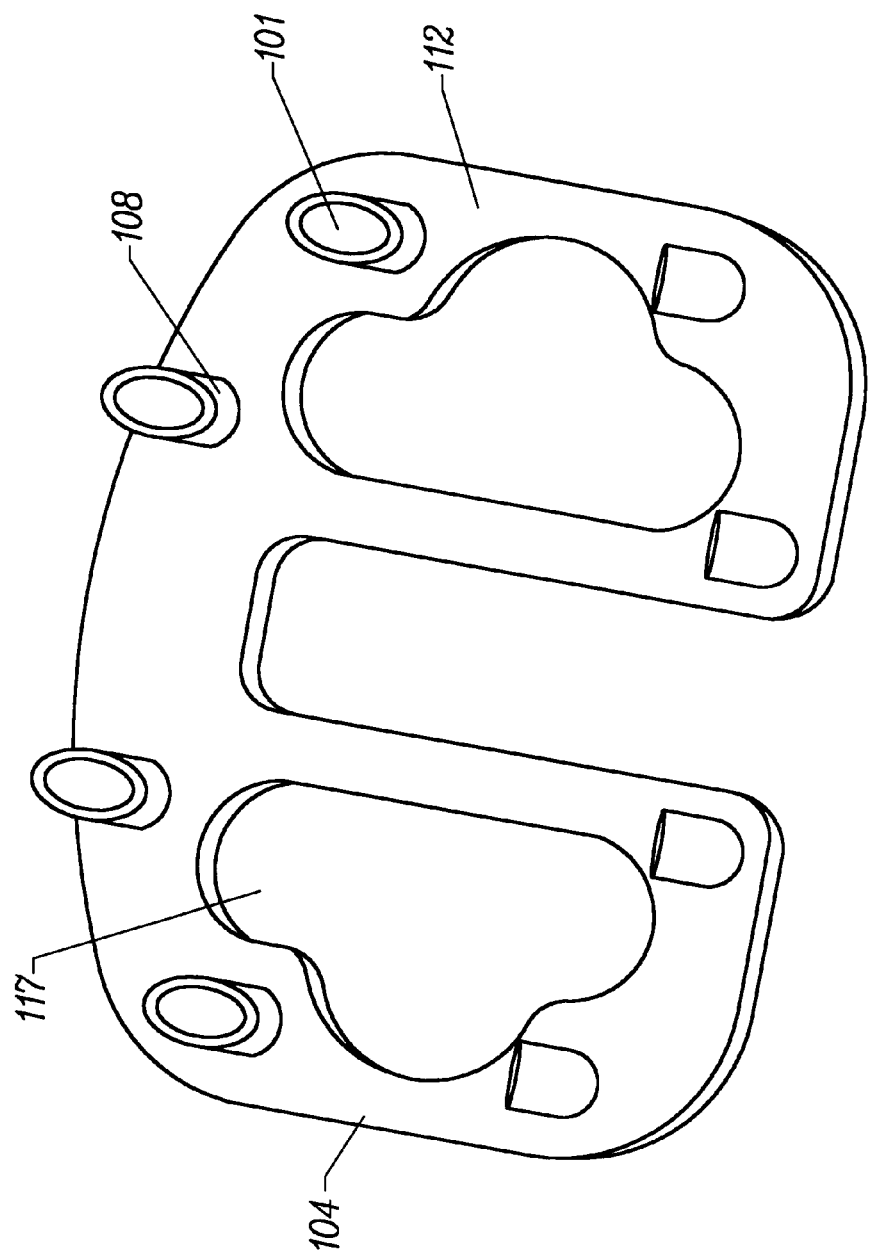

FIG. 5C illustrates the first anchor plate 104 included in the implantable device 100. A plurality of anchoring elements 108 extend substantially vertically from a plate member 112. The anchor plate 104 have hollow bores 117 to form part of channel 103 and recessed portion configured to be accommodated within the cage 102 and to receive force applied to introduce the anchoring elements 108 into the end plates of adjacent vertebrae.

Figure 5D:
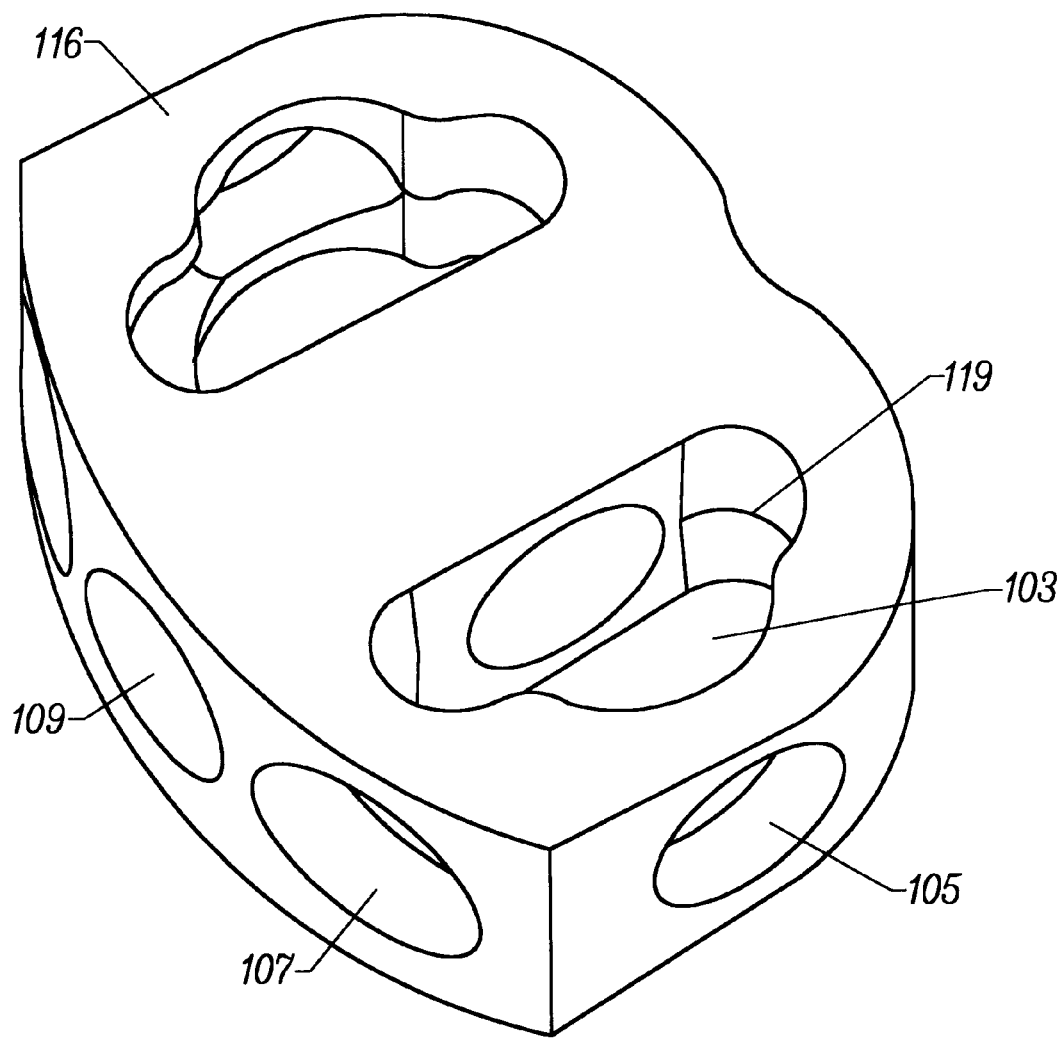

FIG. 5D illustrates a spacer 116 included in the cage of the implantable device 100. The hollow bores 119 form part of the channels 103, 105, 107 and 109.

Figure 5E:
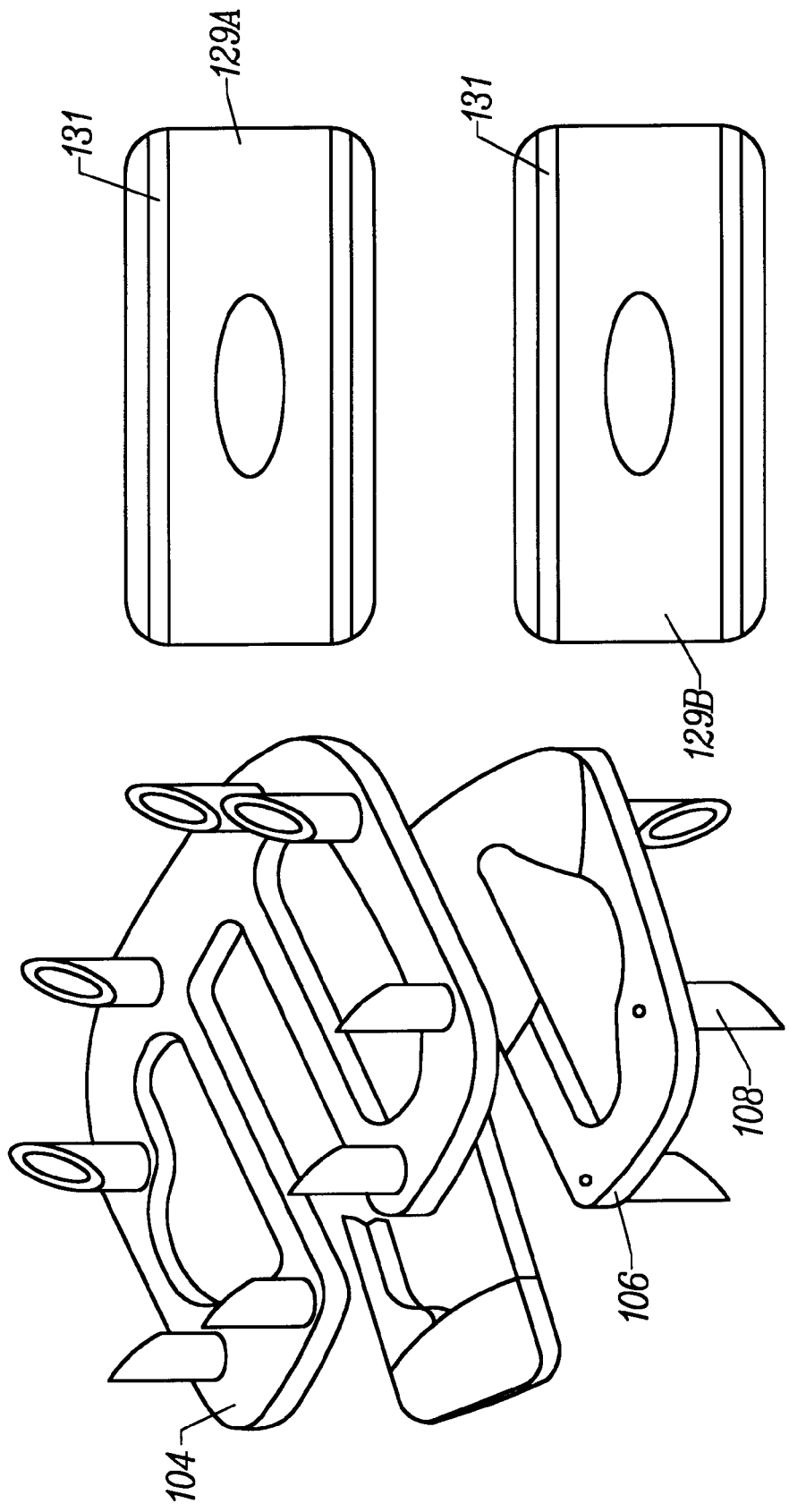
FIG. 5E illustrates a disassembled implantable device with opposing anchor plates and sidewalls for maintaining a separation between the anchor plates.
Figure 5F:
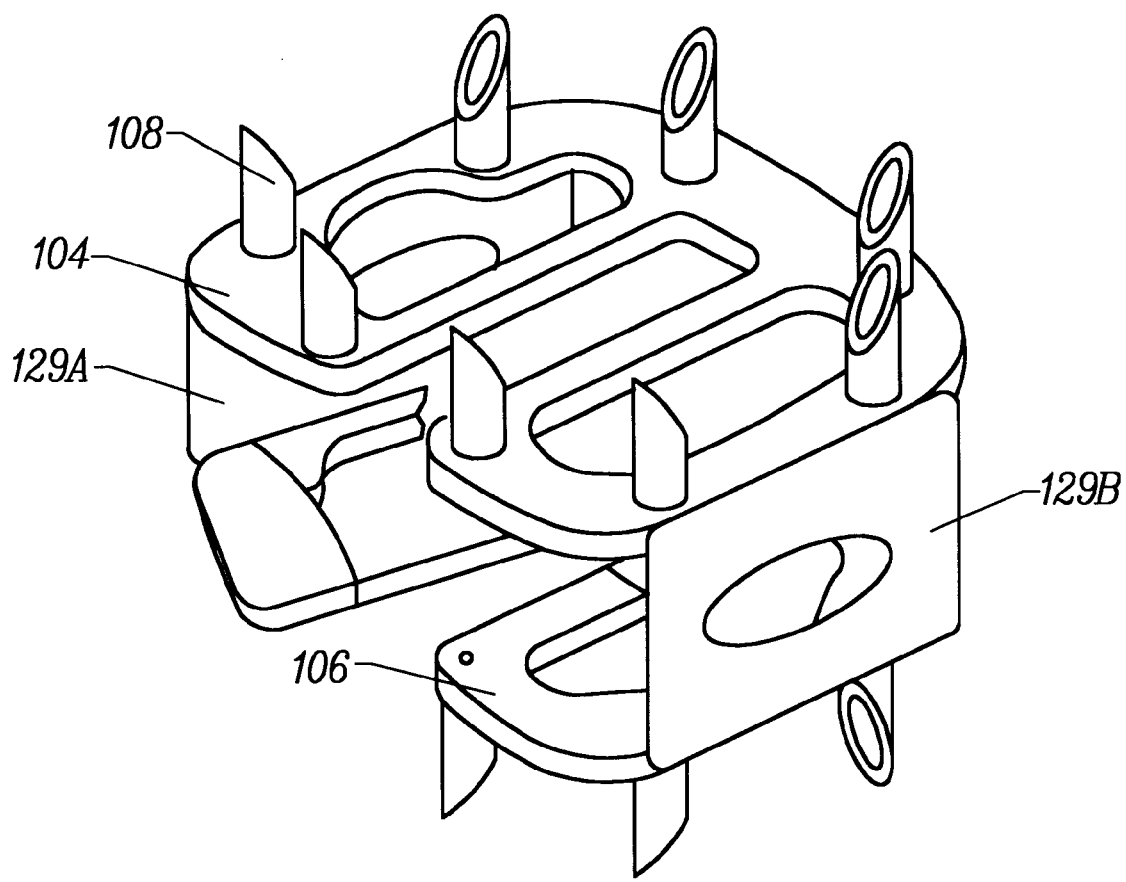
FIG. 5F illustrates side view of an assembled implantable device with opposing anchor plates and sidewalls for maintaining a separation between the anchor plates.
Figure 5G:
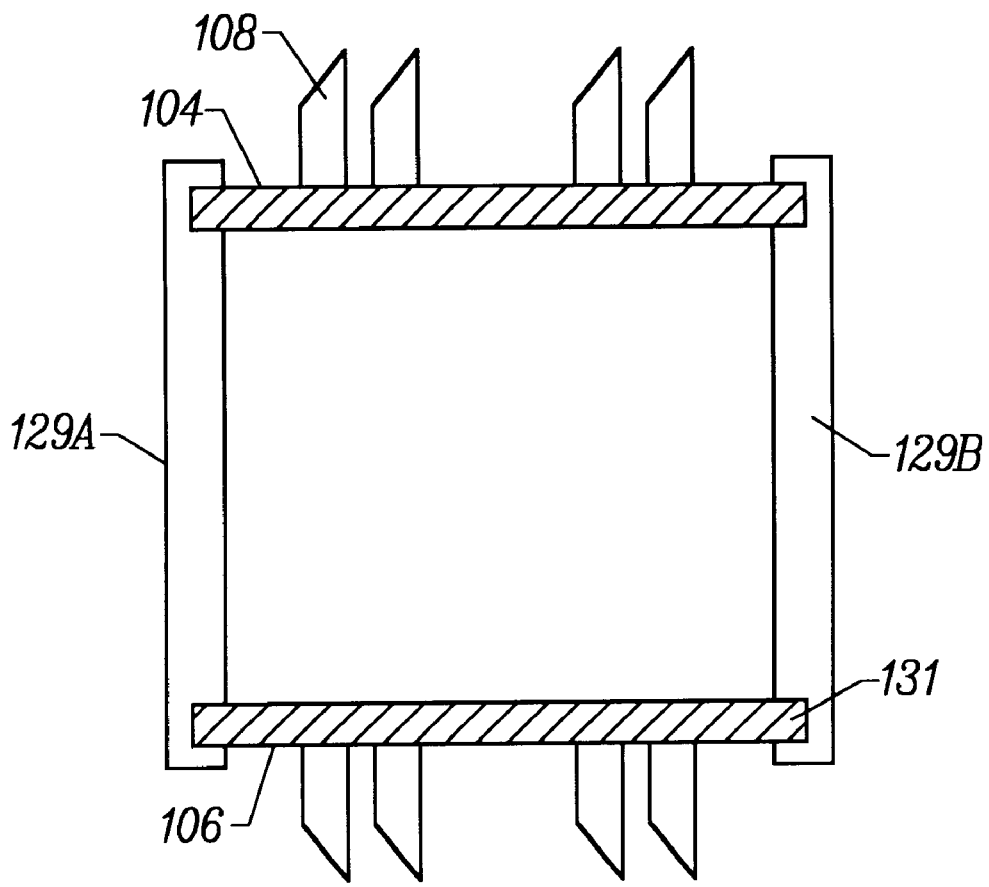
FIG. 5G illustrates another side view of an assembled implantable device with opposing anchor plates and sidewalls for maintaining a separation between the anchor plates.

FIGS. 5E–G illustrate an alternate embodiment of an implantable device with opposing anchor plates and sidewalls for maintaining a separation between the anchor plates. FIG. 5E illustrates the device disassembled with two opposing anchor plates 104,106 and two sidewall support members 129A and 129B. The sidewall support members each include recessed grooves 131 for attaching the sidewall support members to the anchor plates.

FIGS. 5F and 5G illustrate side views of the device illustrated in FIG. 5E once assembled. Assembly is achieved by attaching each sidewall support member to a side of the anchor plates. The device illustrated in FIGS. 5E–G have an advantage of being smaller than the devices illustrated in FIGS. 5A–5D since the sidewall spacers remove the need for the cage.

Figure 6:
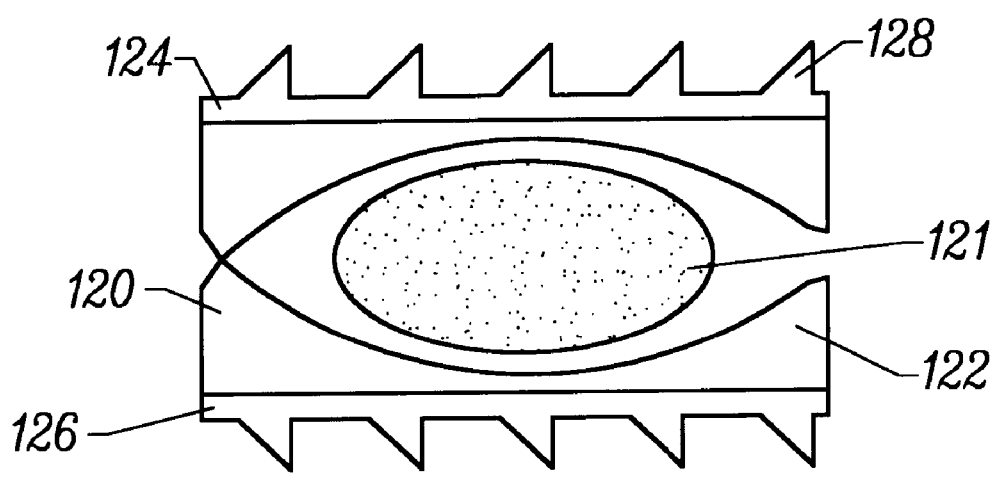
FIG. 6 illustrates an implantable device containing an artificial intervertebral disc.

FIG. 6 illustrates an embodiment of an artificial disc 120. As illustrated in FIG. 6, oval-shaped nucleus 121 made of ceramic or stainless steel is housed inside of the cage 122. Anchoring elements 128 extend from the anchor plates 124 and 126 and can be introduced into the end plates of adjacent vertebrae, thereby replacing the damaged and/or malfunctioning disc with an artificial one.

Figure 7A:
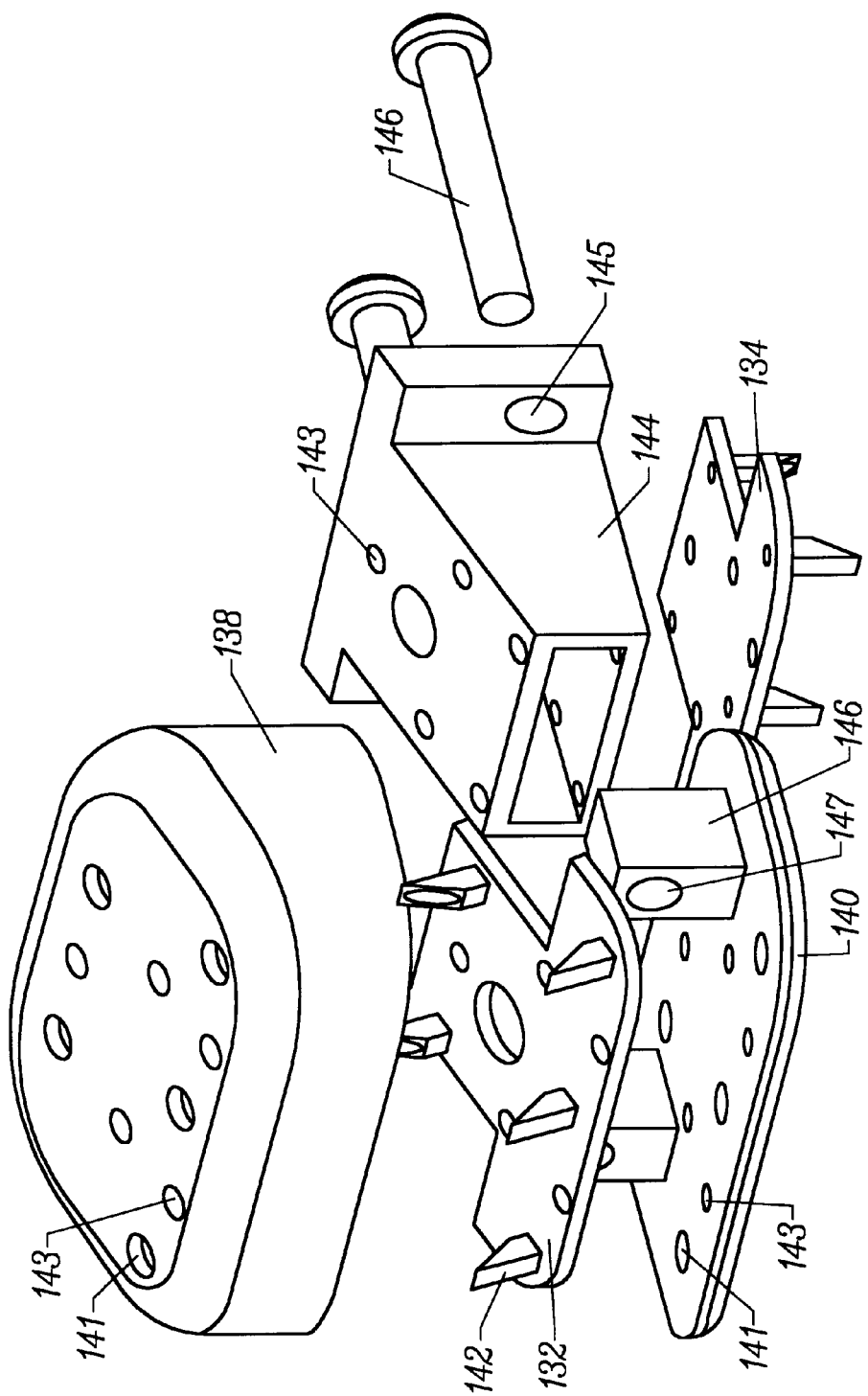
FIG. 7A is a frontal view of the assembly of an implantable device.
Figure 7B:
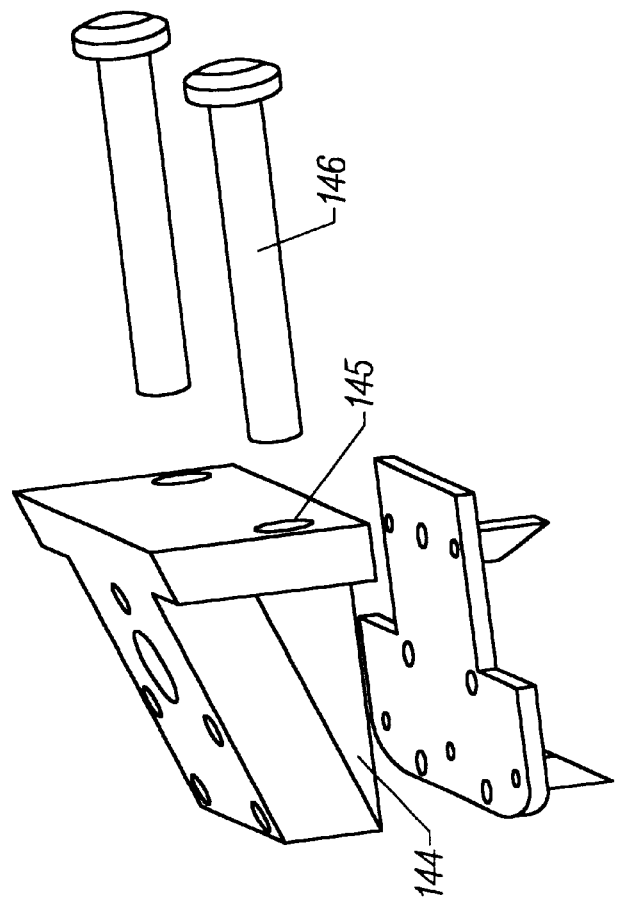
FIG. 7B is a side view of the assembly of an implantable device.
Figure 7B:
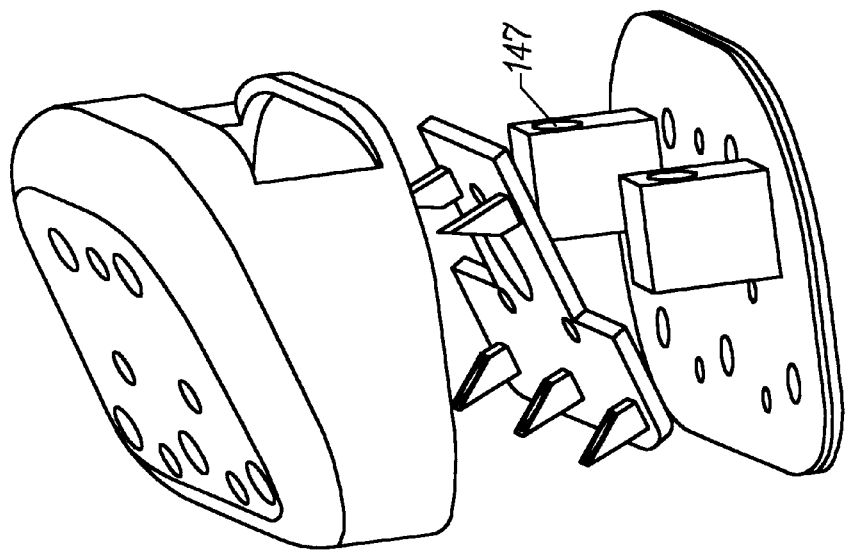
Figure 7C:
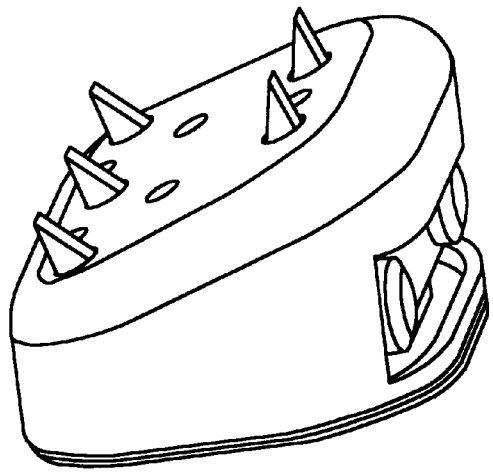
FIG. 7C illustrates the assembled implantable device.
Figure 7D:
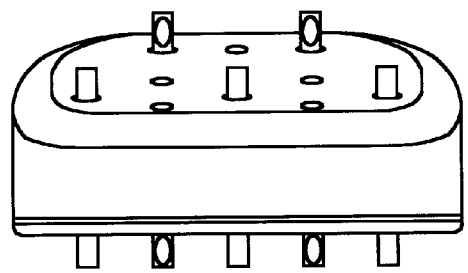
FIG. 7D is a rear view of the assembled implantable device.
Figure 7E:
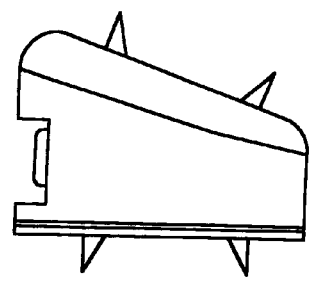
FIG. 7E is a side view of the assembled implantable device.

Details of the assembly of an embodiment of an implantable device are illustrated in FIGS. 7A–C. According to this embodiment, the implantable device 130 includes a first anchor plate 132, a second anchor plate 134, and a cage comprising an upper cover 138 and a bottom plate 140 (FIG. 7A). The first and second anchor plates 132 and 134 are adapted to fit into the cage with a portion of the plates flanked by two supporting members 146. The anchoring elements 142 on the anchor plate are positioned through the hole 141 on the upper cover 138 and bottom plate 140. As illustrated in FIG. 7B showing a side view of the assembly, a wedge 144 is inserted between the upper cover 138 and bottom plate 140 of the cage 136. Through a channel formed by holes 145 and 147, a fixation screw 146 can be used to drive the wedge 144 which pushes the anchor plates 132 and 134 toward end plates of adjacent vertebrae, thereby introducing the anchoring elements 142 into the end plates and securing the device 130 intradiscally. Further, as illustrated in FIG. 7C showing the assembled implantable device 130, there are also a plurality of holes 143 throughout the anchor plates, the upper cover 138 and the bottom plate 140 to allow bone ingrowth through the device 130 to enhance intervertebral fusion.

FIG. 7F illustrates assembly of the implantable device illustrated in FIGS. 5A–D.

A method is also provided for anchoring an implantable device within an intradiscal section between adjacent vertebrae which includes:

creating a space between adjacent vertebrae;

inserting into the space created an implantable device comprising an anchor plate comprising of a plate member sized to be positioned within the space and a plurality of anchoring elements extending from a surface of the plate member, each anchoring element including a distal portion capable of being introduced into an end plate of one of the adjacent vertebrae; and causing the anchoring elements on the anchor plate to be introduced into the vertebrae through the vertebral end plate.

Another method is provided for anchoring an implantable device within an intradiscal section between adjacent vertebrae which includes:

creating a space between adjacent vertebrae;

inserting into the space created an implantable device comprising a first anchor plate comprising of a plate member sized to be positioned within the space and a plurality of anchoring elements extending from a surface of the plate member, each anchoring element including a distal portion capable of being introduced into an end plate of one of the adjacent vertebrae;

a second anchor plate comprising of a plate member sized to be positioned within the space and a plurality of anchoring elements extending from a surface of the plate member, each anchoring element including a distal portion capable of being introduced into an end plate of one of the adjacent vertebrae; and causing the anchoring elements on the first and second anchor plates to be introduced into the vertebrae through the vertebral end plate.

Figure 8A:
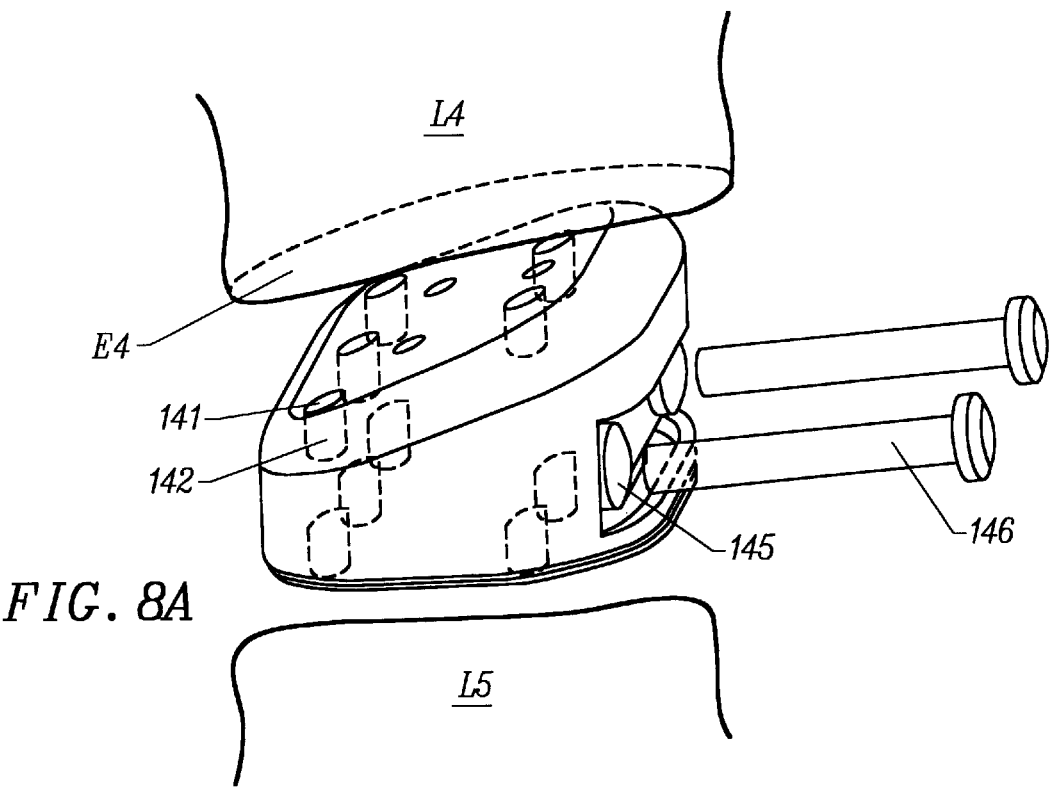
FIG. 8A illustrates an implantable device of FIGS. 7A–E inserted in an intradiscal space prior to extension of anchoring elements.
Figure 8B:
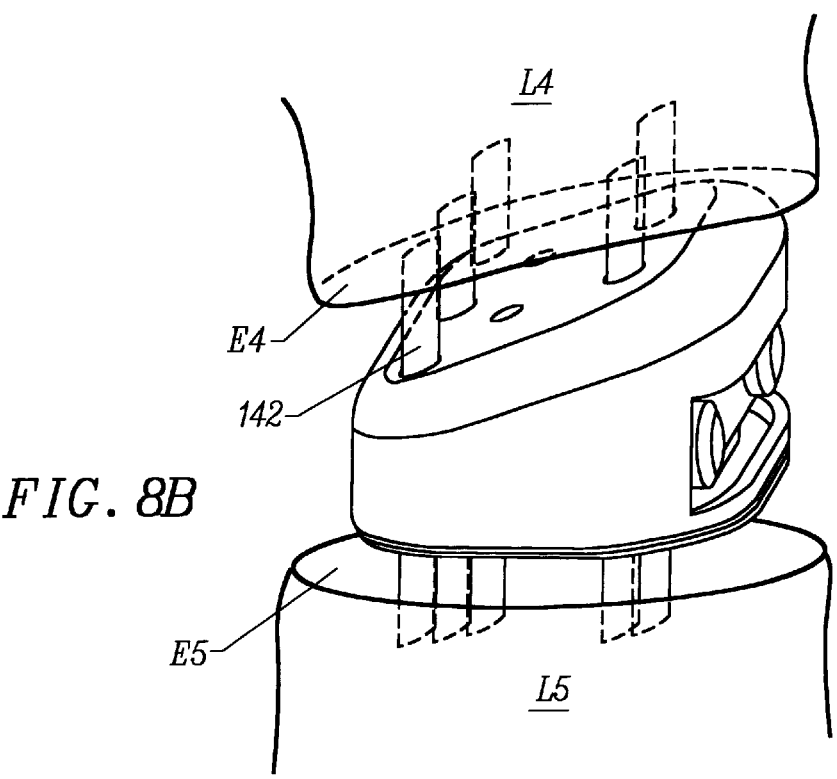
FIG. 8B illustrates the implantable device of FIGS. 7A–E where the anchoring elements have been extended into the end plates of adjacent vertebrae.

As illustrated in FIG. 8A, the anchoring elements 142 of first (132) and second (134) anchor plates of an implantable device 130 illustrated in FIGS. 7A–E are introduced into the vertebrae by applying a force with fixation screws 146 to the anchor plates approximately perpendicular to a plane of the end plate such as E4 and E5 of vertebrae L4 and L5, respectively. FIG. 8B shows that the implantable device 130 is anchored between the adjacent vertebrae L4 and L5 by the anchoring elements 142 penetrating vertebral end plates E4 and E5.

As also illustrated in FIGS. 8A and 8B, the anchoring elements 142 are introduced into the vertebrae L4 and L5 without rotating the anchor elements 142. Screwing an element into a vertebra can cause the vertebra to splinter.

As also illustrated in FIGS. 8A and 8B, the anchoring elements are introduced into the vertebrae without first creating one or more holes in the vertebrae for the anchoring elements.

In yet another embodiment according to the method, the implantable device includes an intradiscal component. Examples of intradiscal components include an intradiscal spacer, a cage, and an artificial disc.

In yet another embodiment according to the method, the implantable device includes first and second anchor plates, inserting including positioning the first anchor plate adjacent a first of the adjacent vertebra and positioning the second anchor plate adjacent a second of the adjacent vertebra, and causing the anchoring elements to be introduced into the vertebrae including causing anchoring elements on the first anchor plate to be introduced into the first vertebra and causing anchoring elements on the second anchor plate to be introduced into the second vertebra.

Figure 9B:
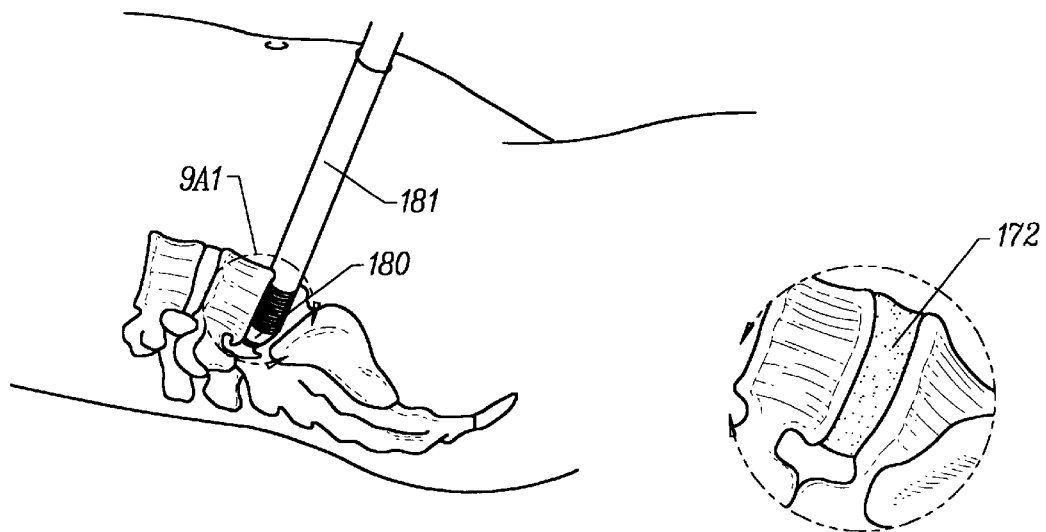
Figure 9B:
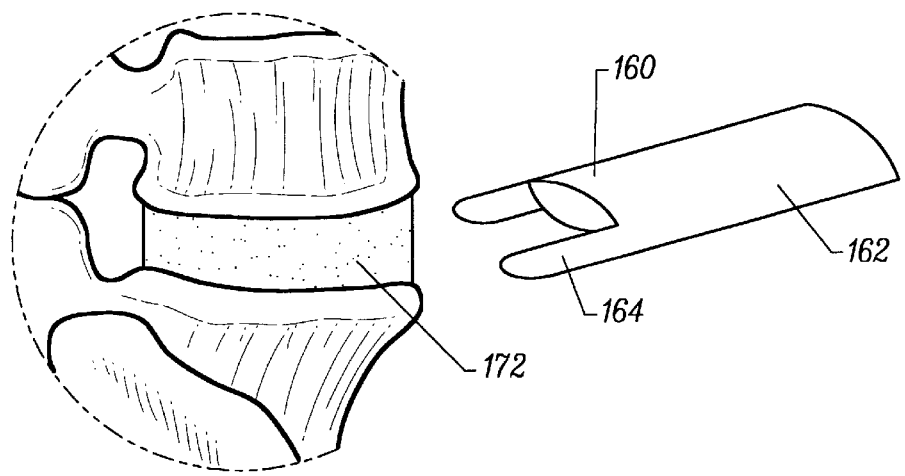
Figure 9C:
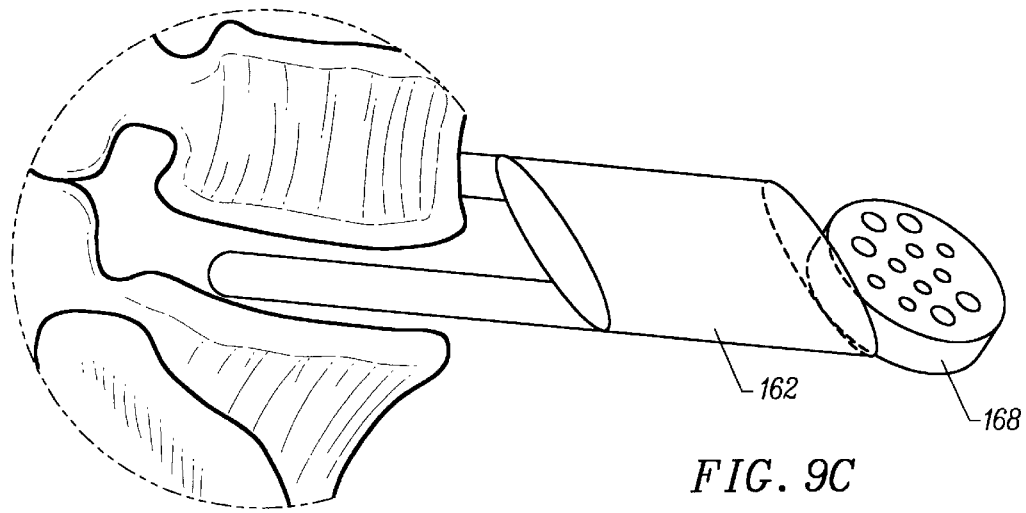
Figure 10:
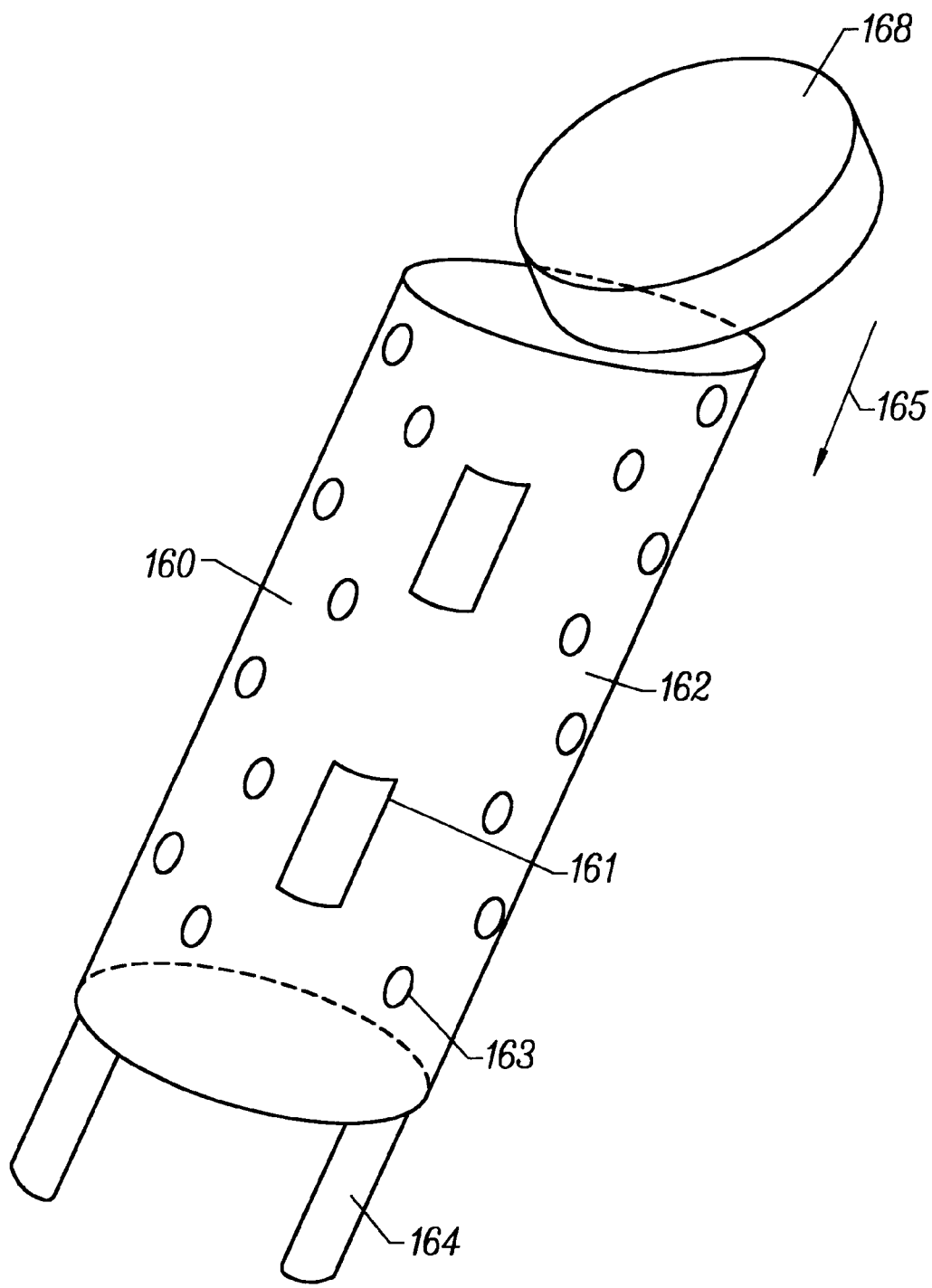
FIG. 10 illustrates an example of a guide used in the method described in FIGS. 9A–D.

FIGS. 9A–9C illustrate a method for introducing a device according to the present invention by an anterior approach. FIG. 10 illustrates a guide employed in the method.

As illustrated in FIG. 10, a guide 160 includes a sleeve 162 and at least two lips 164 that can be inserted intradiscally to maintain the height of the disc space. The sleeve 162 is preferably cylindric with an elliptical cross section 167, and has multiple vents 161 and 163 for proper circulation of air. A replacement disc 168 can be introduced into the intradiscal space through the sleeve 162 in a direction 165 approximately along a longitudinal axis of the sleeve.

FIGS. 9A–D illustrate a method for implanting a device via anterior approach. As illustrated in FIG. 9A, an intervertebral disc 180 to be replaced is accessed through a laparoscopic anterior approach. The disc 180 is exposed anteriorly, i.e. beneath the chest and abdomen of the patient. After the disc 180 to be removed has been identified, the disc is surgically removed. To prepare the adjacent vertebrae to receive the disc replacement 168, cartilage on the end plates of the adjacent vertebrae is removed by an instrument 181 following known procedures. Care should be taken not to violate the end plates. One or two spacers 172 are then inserted into the intradiscal space, with the adjacent vertebrae being separately distracted by a wedge so as to allow proper location of the spacer 172. The spacer 172 also serves as a measurement of the height of the disc space.

Figure 9D:
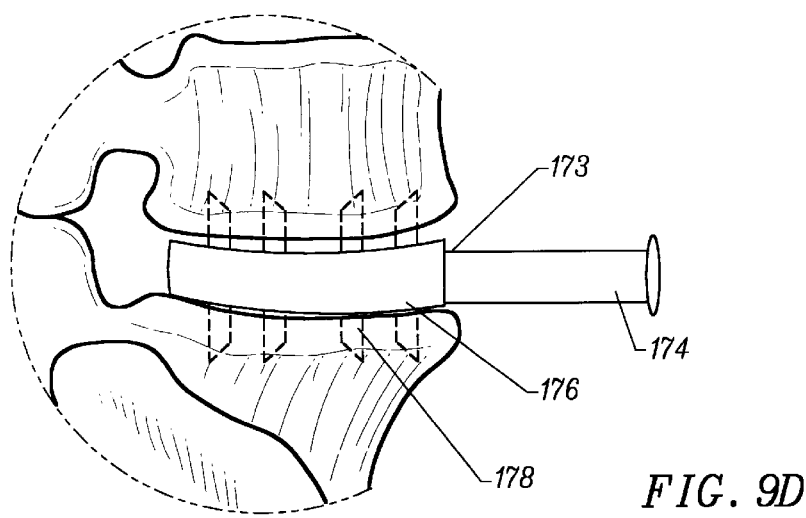

As illustrated in FIG. 9B, a guide 160 (described in regard to FIG. 10) is put over the spacers 172 with the lips 164 of the sleeve 162 replacing the spacers 172. The spacers 172 are then removed from the disc space. As illustrated in FIG. 9C, once the disc replacement guide sleeve 160 is properly positioned, an implantable device such as a replacement disc 168, is inserted through the sleeve 162 into the interdiscal space. As illustrated in FIG. 9D, a wedge spreader 174 is then inserted into a channel 173 defined by the implantable device to distract the anchor plates 176 and introduce anchoring elements 178 on the anchor plates 176 into the end plates of the adjacent vertebrae.

While the present invention is disclosed by reference to the various embodiments and examples detailed above, it should be understood that these examples are intended in an illustrative rather than limiting sense, as it is contemplated that modifications will readily occur to those skilled in the art which are intended to fall within the scope of the present invention.

What is claimed is:

1. An implantable device for insertion into an intradiscal section between adjacent vertebrae, the device comprising:

an anchor plate comprising a plate member sized to be positioned within an intradiscal section between adjacent vertebra and a plurality of anchoring elements extending from a surface of the plate member, each anchoring element including a distal portion capable of being introduced into an end plate of one of the adjacent vertebrae; and an intradiscal component coupled to the anchor plate, the intradiscal component including a cage having a first side for positioning adjacent a first vertebra and a second side for positioning adjacent a second vertebra, the first side including a plurality of holes through which the anchoring elements on the anchor plate can be positioned, and the second side including at least one hollow bore.

2. An implantable device according to claim 1 wherein the anchor plate includes at least 3 anchoring elements.

3. An implantable device according to claim 1 wherein the anchor plate has a non-smooth surface.

4. An implantable device according to claim 1 wherein the anchor plate has at least one hollow bore.

5. An implantable device according to claim 1 wherein at least one of the anchoring elements includes a lumen.

6. An implantable device according to claim 1 wherein at least one of the anchoring elements includes a lumen at least 0.5 mm in diameter.

7. An implantable device according to claim 1 wherein the anchoring elements extend substantially perpendicular from the anchor plate.

8. An implantable device according to claim 1 wherein the anchoring elements extend angularly from the anchor plate.

9. An implantable device according to claim 1 wherein the anchoring elements have at least one curved distal end.

10. An implantable device according to claim 1 wherein the anchoring elements have a smooth outer surface.

11. An implantable device according to claim 1 wherein the anchoring elements do not include a thread for screwing the anchoring element into the vertebrae.

12. An implantable device according to claim 1 wherein the intradiscal component includes an artificial disc.

13. An implantable device according to claim 1 wherein the intradiscal component further includes at least one channel adapted to receive bone graft material therein.

14. An implantable device according to claim 1 wherein the intradiscal component includes a spacer.

15. An implantable device according to claim 1 wherein the anchoring elements include a distal portion capable of piercing an end plate of a vertebrae which does not already have holes for the anchoring elements.

16. An implantable device for insertion into an intradiscal space between adjacent vertebra, the device comprising:

a first anchor plate comprising a plate member sized to be positioned within an intradiscal section between adjacent vertebra and a plurality of anchoring elements extending from a surface of the plate member, each anchoring element including a distal portion capable of being introduced into an end plate of one of the adjacent vertebrae;

a second anchor plate comprising a plate member sized to be positioned within an intradiscal section between adjacent vertebra and a plurality of anchoring elements extending from a surface of the plate member, each anchoring element including a distal portion capable of being introduced into an end plate of one of the adjacent vertebrae; and an intradiscal component coupled to the first and second anchor plates, the intradiscal component including a cage having a first side for positioning adjacent a first vertebra and a second side for positioning adjacent a second vertebra, the first side including a plurality of holes through which the anchoring elements on the first anchor plate can be positioned, and the second side including a plurality of holes through which the anchoring elements on the second anchor plate can be positioned.

17. An implantable device according to claim 16 wherein the intradiscal component includes an artificial disc.

18. An implantable device according to claim 16 wherein the intradiscal component further includes at least one channel adapted to receive bone graft material therein.

19. An implantable device according to claim 16 wherein the intradiscal component includes a spacer.

20. An implantable device according to claim 16 wherein the anchoring elements include a distal portion capable of piercing an end plate of a vertebrae which does not already have holes for the anchoring elements.

21. A kit for forming an implantable device for insertion into an intradiscal section between adjacent vertebrae, the kit comprising:

an intradiscal component sized to be positioned within an intradiscal section between first and second adjacent vertebrae, the intradiscal component comprising a cage having a first side for positioning adjacent the first vertebra and a second side for positioning adjacent the second vertebra, the first side of the cage including a plurality of holes; and an anchor plate comprising a plate member and a plurality of anchoring elements extending from a surface of the plate member, the anchor plate being positionable within the cage and the anchoring elements being extendable out of the cage through the plurality of holes.

22. A kit according to claim 21 wherein the anchoring elements are adapted to be extended out of the cage in a direction approximately perpendicular to a plane of an end plate of the first vertebra.

23. A kit according to claim 21 wherein the intradiscal component further includes at least one channel adapted to receive bone graft material therein.

24. A kit according to claim 21 wherein the intradiscal component further includes at least one channel adapted to receive a device for causing the anchoring elements to be introduced into an end plate of the first vertebra.

25. A kit according to claim 21 wherein the anchoring elements include a distal portion capable of piercing an end plate of a vertebrae which does not already have holes for the anchoring elements.

26. A kit for forming an implantable device for insertion into an intradiscal section between adjacent vertebrae, the kit comprising:

an intradiscal component sized to be positioned within an intradiscal section between first and second adjacent vertebrae, the intradiscal component comprising a cage having a first side for positioning adjacent the first vertebra and a second side for positioning adjacent the second vertebra, the first and second sides of the cage including a plurality of holes;

a first anchor plate comprising a plate member and a plurality of anchoring elements extending from a surface of the plate member, the first anchor plate being positionable within the cage and the anchoring elements being extendable out of the cage through the plurality of holes on the first side of the cage; and a second anchor plate comprising a plate member and a plurality of anchoring elements extending from a surface of the plate member, the second anchor plate being positionable within the cage and the anchoring elements being extendable out of the cage through the plurality of holes on the second side of the cage.

27. A kit according to claim 26 wherein the anchoring elements of the first and second anchor plates are adapted to be extended out of the cage in a direction approximately perpendicular to end plate surfaces of the first and second vertebrae.

28. A kit according to claim 26 wherein the intradiscal component further includes at least one channel adapted to receive bone graft material therein.

29. A kit according to claim 26 wherein the intradiscal component further includes at least one channel adapted to receive a device for causing the anchoring elements to be introduced into end plates of the first and second vertebrae.

30. A kit according to claim 26 wherein the anchoring elements include a distal portion capable of piercing an end plate of a vertebrae which does not already have holes for the anchoring elements.

31. A method for anchoring an implantable device within an intradiscal section between adjacent vertebrae, the method comprising:

creating a space between the adjacent vertebrae;

inserting into the space created an implantable device comprising a first anchor plate comprising a plate member sized to be positioned within the space and a plurality of anchoring elements extending from a surface of the plate member, each anchoring element including a distal portion capable of being introduced into an end plate of one of the adjacent vertebrae, a second anchor plate comprising a plate member sized to be positioned within the space and a plurality of anchoring elements extending from a surface of the plate member, each anchoring element including a distal portion capable of being introduced into an end plate of one of the adjacent vertebrae, and an intradiscal component coupled to the first and second anchor plates; and causing the anchoring elements on the first and second anchor plates to be introduced into the adjacent vertebrae through each of the vertebral end plates by applying a force to the anchor plate approximately perpendicular to a plane of the end plate so as to cause the anchoring elements on the anchor plate to be introduced into the vertebra through the vertebral end plate.

32. A method for anchoring an implantable device within an intradiscal section between adjacent vertebrae, the method comprising:

creating a space between the adjacent vertebrae;

inserting into the space created an implantable device comprising a first anchor plate comprising a plate member sized to be positioned within the space and a plurality of anchoring elements extending from a surface of the plate member, each anchoring element including a distal portion capable of being introduced into an end plate of one of the adjacent vertebrae, a second anchor plate comprising a plate member sized to be positioned within the space and a plurality of anchoring elements extending from a surface of the plate member, each anchoring element including a distal portion capable of being introduced into an end plate of one of the adjacent vertebrae, and an intradiscal component coupled to the first and second anchor plates; and causing the anchoring elements on the first and second anchor plates to be introduced into the adjacent vertebrae through each of the vertebral end plates without first creating one or more holes in the vertebrae for the anchoring elements.

* * * * *